United States Patent
Larisch et al.

(10) Patent No.: US 8,372,589 B2
(45) Date of Patent: Feb. 12, 2013

(54) METHODS FOR THE DIAGNOSIS AND PROGNOSIS OF LEUKEMIA AND OTHER CANCER TYPES

(76) Inventors: Sarit Larisch, Zichron-Yaakov (IL); Ronit Elhasid, Tel-Aviv (IL)

( * ) Notice: Subject to any disclaimer, the term of this patent is extended or adjusted under 35 U.S.C. 154(b) by 0 days.

(21) Appl. No.: 13/098,466

(22) Filed: May 1, 2011

(65) Prior Publication Data
US 2012/0107821 A1    May 3, 2012

Related U.S. Application Data

(63) Continuation-in-part of application No. 10/485,910, filed on Feb. 5, 2004, now abandoned.

(51) Int. Cl.
*C12Q 1/68*    (2006.01)
*G01N 33/53*    (2006.01)

(52) U.S. Cl. .............. 435/6.12; 435/7.1; 435/6.14
(58) Field of Classification Search ............... None
See application file for complete search history.

(56) References Cited

U.S. PATENT DOCUMENTS
2003/0124571 A1\* 7/2003 Larisch et al. ................ 435/6

FOREIGN PATENT DOCUMENTS
WO    WO 0155209 A2 \*  8/2001

\* cited by examiner

*Primary Examiner* — Michael Burkhart

(57) ABSTRACT

Methods for diagnosing leukemia and other cancer types, so that the malignancy thereof dependent on expression of ARTS at low levels or an absence of ARTS expression are disclosed. Moreover methods for prognosis of leukemia and other cancer types, which are prone for an effective treatment by restoring ARTS expression levels and/or restoring cellular ARTS activity are further disclosed.

8 Claims, 3 Drawing Sheets

FIGURE 2: ARTS is not expressed in ALL1 cells; Transfection of ARTS into ALL1 includes apoptosis greatly sensitizing the cells to ara-C treatment.

FIGURE 3
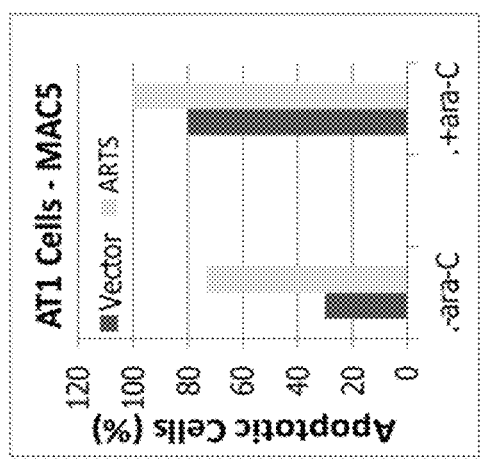
A
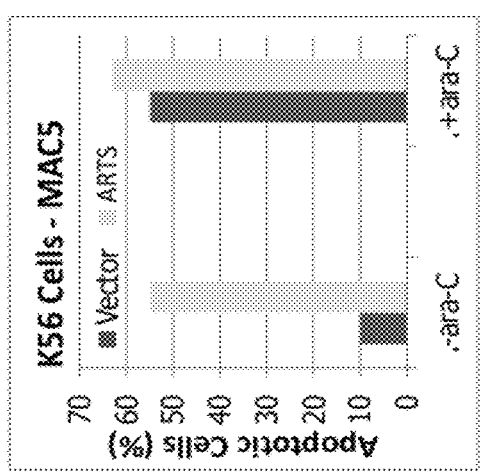
B
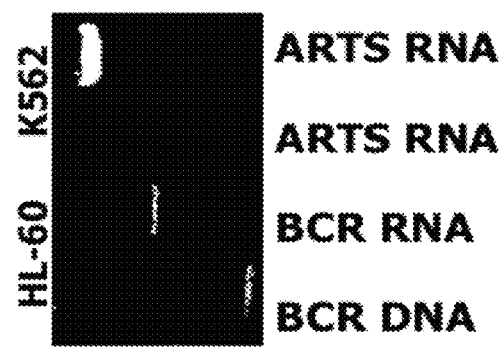
C
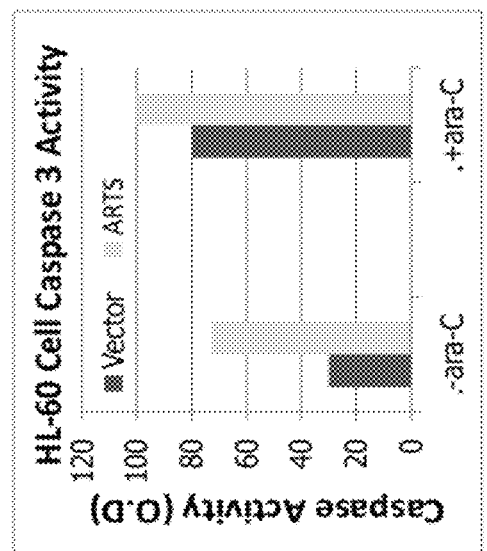

METHODS FOR THE DIAGNOSIS AND PROGNOSIS OF LEUKEMIA AND OTHER CANCER TYPES

CROSS-REFERENCE TO RELATED APPLICATIONS

The present application is a continuation-in-part of U.S. application Ser. No. 10/485,910 filed Feb. 5, 2004 now abandoned, entitled METHODS FOR THE TREATMENT AND PROGNOSIS OF LEUKEMIA AND OTHER CANCER TYPES.

TECHNICAL FIELD

Generally, this invention relates to methods of performing diagnosis and prognosis of leukemia and other cancer types. More particularly this invention relates to methods for diagnosing leukemia and other cancer types, wherein the malignancy thereof is dependent upon expression of ARTS at low levels or an absence of ARTS expression, as well as to methods for prognosis of leukemia and other cancer types, which are prone for an effective treatment by restoring ARTS expression levels and/or restoring cellular ARTS activity.

BACKGROUND ART

Genetic abnormalities associated with hematological malignancies alter the normal structure and function of genes that control cell growth, differentiation or death either in a positive or negative manner (1). The genes involved can be grouped into two general categories. The first group involves the structural alternation of a normal cellular gene, named proto-oncogen, whose protein product induce uncontrolled proliferation or loss of contact inhibition. The second group consists of genes, whose loss of function is associated with malignant transformation, and are referred to as tumor suppressor genes (2). There are several tumor suppressor genes known to be important in evolution of acute leukemia. Both p15 and p16 have been found to be homozygously deleted in 6% to 28% of B lineage acute lymphoblastic leukemia (ALL) patients, while p16 was found to be deleted in 41% to 83% in T cell ALL (3). Others showed that p16 can be functionally inactivated by either point mutations or hypermethylation of the p16 promoter region (4). Another tumor suppressor gene, retinoblastoma gene, was reported to be inactivated at a low frequency in T cell ALL patients (5). P53 another important tumor suppressor gene, was found to be functionally inactivated in 50% of samples from patients at relapse, suggesting that p53 mutations may be important in disease progression (6). Others hypothesized that loss of a putative tumor suppressor named TEL may promote leukemogenesis by affecting cell growth and/or by altering cell adhesion (7).

Recently, a novel human apoptosis inducing protein (ARTS), which induces cell killing by proapoptotic inducers such as TNF β, Fas, etoposide, arabinoside (ara-c) and TNF α, was identified. ARTS is a member of the septin family of proteins and is encoded by 823 base pair cDNA sequence, encoding a predicted polypeptide of 274 amino acids. ARTS contains a P-loop GTP-binding domain, conserved in different classes of ATP/GTPases, including CED-4 and Apaf-1, which are major regulators of apoptosis.

REFERENCES

1. Vannus H E and Lowell C A. 1994 Blood 83,5-9.
2. Thandla S, Aplan P D. Molecular biology of acute lymphocytic leukemia. 1997 Seminars in Oncology 24,45-56.
3. Hebert J, Cayuela J M, Berkeley J, et al: Candidate tumor-suppressor genes MTS1 (p16$^{ink4}$) and MTS2 (p15$^{Ink4B}$) display frequent homozygous deletions in primary cells from T but not from B-cell lineage acute lymphoblastic leukemias. Blood 84:4038-4046, 1994.
4. Merlo A, Herman J G, Mao L, et al: 5 CpG island methylation is associated with transcriptional silencing of the tumor suppressor p16/CDKN2/MTSI in human cancers. Nature Medicine 1: 686-692,1995.
5. Ahuja H G, Jat P S, Foti A, et al: Abnormalities of the retinoblastoma gene in the pathogenesis of acute leukemia. Blood 78: 3259-3268, 1991.
6. Yeargin J, Cheng J, Haas M. Role of the p53 tumor suppressor gene in the pathogenesis and in the suppression of acute lymphoblastic T-cell leukemia. Leukemia 6: 85S-91S, 1992 (suppl).
7. Fenrick R, Wang L, Nip J, et al: TEL, a putative tumor suppressor, modulates cell growth and cell morphology of ras-transformed cells while repressing the transcription of stromelysin-1. Molecular and cellular biology 20: 5828-5839, 2000.
8. Sarit Larisch, Youngsuk Yi, Rona Lotan, Hedviga Kerner, Sarah Eimerl, W. Tony Parks, Gottfried Yossi, Stephanie Birkey Reffey, Mark P. de Caestecker, David Danielpour, Naomi Book-Melamed, Rina Timberg, Colin Duckett, Robert J. Lechleider, Hermann Steller, Joseph Orly, Seong-Jin Kim & Anita B. Roberts. ARTS, a novel mitochondrial septin-like protein, mediates apoptosis dependent on its P-loop motif. Nature Cell Biology, 2: 915-921, 2000.

SUMMARY OF THE INVENTION

The invention provides a method of distinguishing leukemic and other cancerous cells affected by ARTS expression from leukemic and other cancerous cells which are not affected by ARTS expression.

In another embodiment the present invention provides a method for prognosis of particular leukemia or other cancer type as susceptive to a treatment which alters ARTS expression It should be understood, however, that the eclectically synopsized brief summary supra is not to limit the invention to the particular forms and examples, but on the contrary, is to cover all modifications, equivalents, and alternatives falling within the scope of the invention.

The term "low level, or low amounts, or basal level, or basal amount of ARTS" refers interchangeably, hereinafter in the claims and the specification to a level of ARTS protein which is two to ten-fold lower than the level of ARTS protein presented in a non malignant cell, such as for example, cell derived from healthy volunteer, or to cell that do not express ARTS at all, as determined by immunohistochemical methods for detecting protein level.

The term "does not express or contain ARTS" means hereinafter in the Specification and in the Claims section that the cell express or contain either low level of ARTS protein or RNA that can be hardly detected by the existing immunohistochemistry methods or by the methods of measuring RNA, or that ARTS protein or RNA levels in the cells is between two to twenty fold less than the level exist in a normal cell.

The term "apoptosis" relates hereinafter to cell death which is characterized by caspase activation and/or annexin-v binding, and/or nuclear condensation and subsequent fragmentation of the DNA in nucleus. Apoptosis can be tested by visualizing the dead cells to identify whether they are shrieked, or using assays and kits which exist in the market for detecting DNA fragmentation, detecting of proteins which are related to Apoptosis such as BCL2 and detecting membrane alterations, such as asymmetry of the plasma membrane.

The term "RNA" refers to an oligonucleic in which the sugar is ribose, as opposed to deoxyribose in DNA. RNA is intended to include any nucleic acid, which can be entrapped by ribosomes and translated into protein. The term "mRNA" refers to messenger RNA. The term "DNA construct" refers hereinabove in the specification and in the claims to any nucleic acid sequence which increases the expression of the ARTS protein in the cell or that cause activation of ARTS protein. The administration of such a DNA construct will result in one embodiment in higher amount of ARTS in the cell mitochondria, cytoplasm and/or nucleus. The term "DNA construct" covers DNA that has the sequence of part or a full sequence of naturally occurring genomic DNA molecule, a separate molecule such as cDNA, a genomic fragment, a fragment produced by a polymerase chain reaction (PCR), a restriction fragment or a recombinant nucleic acid sequence that is a part of a hybrid gene. The length of the probe can be 20 to 80 bases.

DESCRIPTION OF THE DRAWINGS

The present invention will be understood and appreciated more comprehensively from the following detailed description taken in conjunction with the appended drawings in which.

Figure 1:
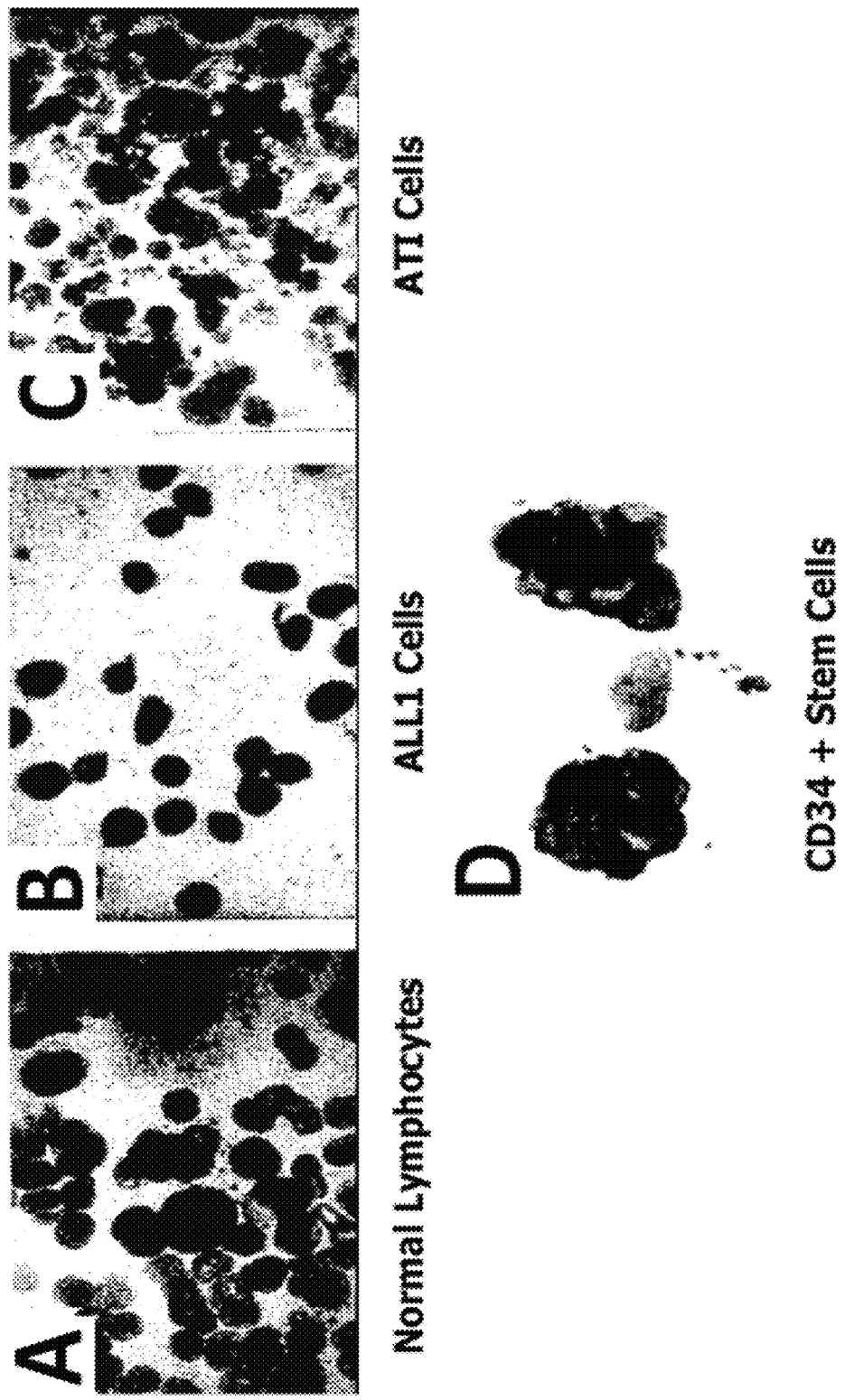
FIG. 1 demonstrates the ARTS protein is absent in certain leukemic cells, yet present in hematopoetic stem cells. Immunhistochemistry results using anti-ARTS specific polyclonal antibody on normal lymphocytes (1A) ALL 1 cells (1B) AT1 cells (1C) and CD34+ stem cells (1D) showing the expression of ARTS in normal lymphocytes, AT1 and CD34+ stem cells. ARTS protein is not expressed in ALL 1 leukemic cells (1B).

ALL 1 cells transfected with either empty vector or ARTS, −/+ treatment with ara-C were incubated with annexin-V coated magnetic beads and separated using appropriate columns (Macs, Mitenyi-Biotec). Number of alive or apoptotic cells (x106) counted is presented in 2C.

FIG. 3 shows that overexpression of ARTS induces apoptosis in leukemic cells: transfection of ARTS into K562, AT1, and HL-60 cells induces apoptosis. In all cell lines. The ability of ARTS to induce apoptosis, is at least equal to the effect of ara-C alone in all tested cells. In both AT1 and HL-60 cells the effect of ARTS alone was higher then ara-C. In all cells apoptosis was more pronounced when the cells were both transfected with ARTS and treated with ara-C. Kinetics of apoptosis was measured 24, 36 and 48 hours after transfection in K562 cells, and ara-C was added for two and four hours in each time point. Maximum effect of ARTS with ara-C was seen after two hours of treatment. RT-PCR results in HL-60 cells showing that ARTS RNA is absent in these cells, as compared to ARTS RNA present in K562 cells (3C) BCR, genomic DNA and RNA were shown to be present in HL-60 cells, as controls for the presence of DNA and RNA in this assay. Each graph represents the average results of 3 experiments done in duplicates.

While the invention is susceptible to various modifications and alternative forms, specific embodiments thereof have been shown merely by way of example in the drawings. The drawings are not necessarily complete and components are not essentially to scale; emphasis instead being placed upon clearly illustrating the principles underlying the present invention.

DETAILED DESCRIPTION OF EMBODIMENTS

The invention is based on the unexpected findings obtained in cells derived from leukemic patients showing either complete absence of both the ARTS protein and the ARTS RNA in these cells, or basal level of the ARTS protein and the ARTS RNA. Thus, based on the finding that ARTS is functioning as a tumor suppressor gene.

ARTS is a novel human apoptosis related protein which is a member of the septin family of proteins and possesses unique C-terminus and which effectively mediates apoptosis and modulates the actions of TGF-13 on cells. The ARTS amino sequence is as follows:

TABLE 1

ARTS Protein Amino Acid Sequence

SEQ. ID. No. 1:
MIKRFLEDTT DDGELSKFVK DFSGNASCHP PEAKTWASRP

QVPEPRPQAP DLYDDDLEFR PPSRPQSSDN QQYFCAPAPL

SPSARPRSPW GKLDPYDSSE DDKEYVGFAT LPNQVHRKSV

KKGFDFTLMV AGESGLGKST LVNSLFLTDL YRDRKLLGAE

ERIMQTVEIT KHAVDIEEKG VRLRLTIVDT PGFGDAVNNT

ECWKPVAEYI DQQFEQYFRD ESGLNRKNIQ DNRVHCCLYF

ISPFGHGYGP SLRLLAPPGA VKGTGQEHQG QGCH

The ARTS protein is located in the mitochondria and in certain cells the apoptotic induction is correlated with translocation of ARTS to the nucleus during the apoptotic process. The method of inducing apoptosis is based on the unexpected dramatic data showing that cells derived from leukemic subjects express less ARTS protein or do not express at all ARTS protein. This was exemplified in Example 4, where leukemic cells lines that were transfected with ARTS have demonstrated apoptosis in contrast to cells that were transfected with empty vectors.

The term "protein" or the "peptide" refer in the claims and in the specification to ARTS protein and variants of the ARTS protein. The variants include any amino acid sequence, in any length from 5-20 amino acids derived from the amino acid sequence provided in SEQ. ID. No. 1. For Example without being limited, the peptide can be:

LPNQVHRKSV KKGFDFTLMV,
or

LVNSLFLTDL,
or

-continued

MIKRFLEDT or

DFSGNASCHP PEAKTWAS or

KHAVDI.

In another embodiment the "DNA construct" is a nucleic acid sequence encoding ARTS variants or ARTS from different species. The nucleic acid sequence encoding ARTS is set forth in SEQ. ID. No. 2

SEQ. ID. No. 2

```
A TGATCAAGCG TTTCCTGGAG GACACCACGG ATGATGGAGA

ACTGAGCAAG TTCGTGAAGG ATTTCTCAGG AAATGCGAGC

TGCCACCCAC CAGAGGCTAA GACCTGGGCA TCCAGGCCCC

AAGTCCCGGA GCCAAGGCCC CAGGCCCCGG ACCTCTATGA

TGATGACCTG GAGTTCAGAC CCCCCTCGCG GCCCCAGTCC

TCTGACAACC AGCAGTACTT CTGTGCCCCA GCCCCTCTCA

GCCCATCTGC CAGGCCCCGC AGCCCATGGG GCAAGCTTGA

TCCCTATGAT TCCTCTGAGG ATGACAAGGA GTATGTGGGC

TTTGCAACCC TCCCCAACCA AGTCCACCGA AAGTCCGTGA

AGAAAGGCTT TGACTTTACC CTCATGGTGG CAGGAGAGTC

TGGCCTGGGC AAATCCACAC TTGTCAATAG CCTCTTCCTC

ACTGATCTGT ACCGGGACCG GAAACTTCTT GGTGCTGAAG

AGAGGATCAT GCAAACTGTG GAGATCACTA AGCATGCAGT

GGACATAGAA GAGAAGGGTG TGAGGCTGCG GCTCACCATT

GTGGACACAC CAGGTTTTGG GGATGCAGTC AACAACACAG

AGTGCTGGAA GCCTGTGGCA GAATACATTG ATCAGCAGTT

TGAGCAGTAT TTCCGAGACG AGAGTGGCCT GAACCGAAAG

AACATCCAAG ACAACAGGGT GCACTGCTGC CTGTACTTCA

TCTCACCCTT CGGCC ATGGG TATGGTCCAA GCCTGAGGCT

CCTGGCACCA CCGGGTGCTG TCAAGGGAAC AGGCCAAGAG

CACCAGGGGC AGGGCTGCCA CTAG
```

In another embodiment the invention provides method of diagnosing and/or predicting hematological malignancy in a subject comprising the steps of:

[i] obtaining a sample from the subject. The sample may be is a lymphocyte, a bone marrow cell or a stem cell.

[ii] contacting said sample with an antibody directed to ARTS protein, thereby to form an antigen-antibody complex;

[iii] detecting the an antigen-antibody complex level, thereby determining the level of said ARTS protein in said sample; and

[iv] Comparing said level of said ARTS to predetermined ARTS protein level of samples derived from healthy Subjects.

The antibodies are agents which can bind to ARTS protein. They can be monoclonal or polyclonal and can be prepared in any mammal. In another embodiment the antibodies can be bound to a radioisotope, fluorescent colorimetric or chemiluminescent compound such as without limitation rhodamine or luciferin or an enzyme such as for example horseredish peroxidase. The cells can be also stained by immunohistochemical methods and visualized then in a microscope.

In another embodiment, serum or intracellular levels of ARTS are assessed, by Enzyme-linked immunosorbent assays (ELISA). An ELISA using anti-ARTS antibodies with a detection limit of preferably about 20 pg/ml in serum, plasma or cell lysate can provide a useful indication of ARTS levels and establish the necessary indication for diagnosis or prognosis. The ELISA is typically performed in accordance with techniques known in the art and described elsewhere. An exemplary protocol for ELISA was includes diluting a serum, plasma or cell lysate to 1 µg/mL in carbonate coating buffer (35 mM sodium carbonate, 15 mM sodium hydrogen carbonate pH 9.6) and coating a 96 well plate (Nunc™, Maxisorp™) overnight at +4C. The plate is then washed three times with wash buffer (0.01M PBS pH 7.2, 0.05% Tween-20) and then three times with 0.01M PBS pH 7.2. The wells are then blocked by adding 200 µl of blocking buffer (1% w/v BSA in 0.01M PBS pH 7.2) to each well and incubating the plate at 25C for 1 hour. The anti-ARTS antibodies are then diluted in antibody diluent (1% w/v BSA, 0.05% Tween-20 in 0.01M PBS pH 7.2) sufficient to generate a titration curve. The wells are incubated with the antibody for 1 hour at 25C. The plate is then washed as previously described. Any secondary antibody-conjugate is then can be used to detect the bound primary antibody. Goat anti-murine immunoglobulin antibody HRP conjugate (Dako) at 1:2000 in antibody diluent and goat anti-human immunoglobulin G (H+L) antibody HRP conjugate (Zymed®) at 1:2000 in antibody diluent can be used to detect bound primary antibodies. After incubation at 25C for 1 hour the plate is washed again as previously described. TMB substrate solution (Zymed®) can be added to each well and the colour allowed to develop; the reaction terminated by adding IM HCl to the wells. The absorbance of each well is determined by spectrophotometry at 450 nm to 620 nm.

In another embodiment, the protein of the cells is extracted. The crude protein is separated for example on SDS PAGE and is than transferred onto nitrocellulose. The resulting Western Blots are screened with a primary antibody which is direct to ARTS and another antibody which bind to the primary antibody and to bound to a radioisotope, fluorescent colorimetric or chemilumiscent compound such as without limitation rhodamine or luciferin or an enzyme such as for example horseredish peroxidase. The Blots are than exposed to a film and the level of thickness or darkness of the bands is detected and compared to the control level derived from healthy volunteers.

In another embodiment there is provided a method of diagnosing and/or predicting a hematological malignancy in a subject comprising the steps of:

[i] obtaining a sample from the subject;

[ii] obtaining cDNA from said sample;

[iii] contacting said cDNA with a specific primer for open reading frame of the ARTS protein so as to form a complex;

[iv] amplifying said complex so as to obtain an amplified product; detecting said amplified product; and

[v] comparing said amplified product level to predetermined amplified product level derived from samples from healthy subjects.

As was demonstrated in Example 3, some of the samples derived from leukemic patients are characterized by the absence of ARTS mRNA. In another embodiment, ARTS mRNA can be measured by southern or northern blot, dot blotting or in-situ hybridization with a labeled probe based on the known sequences of ARTS.

RNA can be extracted from cells or tissues according to methods known in the art. In a preferred embodiment, RNA can be extracted from monolayers of mammalian cells grown in tissue culture, cells in suspension or from mammalian tissue. RNA can be extracted from such sources by, e.g., treating the cells with proteinase K in the presence of SDS. In another embodiment, RNA is extracted by organic solvents. In yet another embodiment, RNA is extracted by differential precipitation to separate high molecular weight RNA from other nucleic acids. RNA can also be extracted from a specific cellular compartment, e.g., nucleus or the cytoplasm. In such methods, the nucleus is either isolated for purification of RNA therefrom, or the nucleus is discarded for purification of cytoplasmic RNA. Further details regarding these and other RNA extraction protocols are set forth, e.g., in Molecular Cloning A Laboratory Manual, 2nd Ed., ed. by Sambrook, Fritsch and Maniatis (Cold Spring Harbor Laboratory Press: 1989).

For instance, RNA can be extracted by a method using guanidium thiocyanate and purification of the RNA on a cesium chloride gradient. Accordingly, tissue or cells are lysed in the presence of guanidium thiocyanate and the cell lysate is loaded on a cushion of cesium chloride (CsCl) and centrifuged at high speed, such that the RNA is recovered in the pellet and the DNA is left in the supernatant after the centrifugation. The RNA can then be recovered by ethanol precipitation. This method is set forth in details, e.g., in Molecular Cloning A Laboratory Manual, 2nd Ed., ed. by Sambrook, Fritsch and Maniatis (Cold Spring Harbor Laboratory Press: 1989).

In order to prevent RNA from being degraded by nucleases, e.g., by RNAases, that may be present, the extraction of RNA, and reactions involving RNA are performed in "RNAase free conditions". Various methods known in the art can be used to maintain RNAase free conditions. For example, during RNA extraction, potent denaturing agents, such as guanidium hydrochloride and guanidium thiocyanate can be used to denature and thereby inactivate nucleases. Reducing agents, e.g., β-mercaptoethanol, can also be used to inactivate ribonucleases. This combination of agents is particularly useful when isolating RNA from tissues rich in ribonucleases, e.g., pancreas (Chirgwin et al. (1979) Biochemistry 18:5294). Other reagents that can be added to a solution containing RNA to prevent degradation of the RNA include RNAase inhibitors, also referred to herein as "protein inhibitor of RNAases", e.g., Rnasin RTM which can be obtained, from Promega Corp. (Madison, Wis.) (e.g., Cat #N2514). Protein inhibitors of RNAases are preferably not included during extraction of RNA using potent denaturing agents (since these will also denature the protein inhibitor of RNAases). However, it is preferable to include such protein inhibitors of RNAases during RNA extraction using more gentle methods of cell lysis and RNAse inhibitors are preferably present at all stages during the subsequent purification of RNA.

Yet another reagent that can be added to a solution containing RNA to prevent degradation of the RNA include vanadyl-ribonucleoside complexes. The complexes formed between the oxovanadium IV ion and any of the four ribonucleosides are transition-state analogs that bind to many RNAases and inhibit their activity almost completely. The four vanadyl-ribonucleoside complexes are preferably added to intact cells and preferably used at a concentration of 10 mM during all stages or RNA extraction and purification. Yet in another embodiment, macaloid is used to absorb RNAases.

In one embodiment, cDNA is synthesized from the mRNA. This step is performed, without being limited, by Reverse Transcriptase Polymerization Chain Reaction (RTIPCR), which produce single stranded DNA molecule using RNA as a template. The technique of reverse transcription can be used to amplify cDNA transcribed from mRNA encoding for secreted and transmembrane proteins. The method of RT/PCR is well known in the art (for example, see Watson and Fleming,) and can be performed as follows: Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end primer. Typically, the primer contains an oligo (dT) sequence.

The cDNA is than contacted with a specific primer for open reading frame of the ARTS protein so as to form a complex. The term "complex" is refer hereinabove in the specification and in the claims section to cDNA which is hybridizes to contacting with a specific primer for open reading frame of the ARTS protein. The complex is then amplified using the PCR method and the above described first and second specific primers. (Belyaysky et al, Nucl Acid Res 17:2919-2932, 1989; Krug and Berger, Methods in Enzymology, Academic Press, N.Y., Vol.152, pp. 316-325, 1987 which are incorporated by reference).

An oligonucleic acid molecule is "hybridizable" to another oligonucleic acid molecule, such as a eDNA, genomic DNA, or RNA, when a single stranded form of the oligonucleic acid molecule can anneal to the other oligonucleic acid molecule under the appropriate conditions of temperature and solution ionic strength (see Sambrook et al.). The conditions of temperature and ionic strength determine the "stringency" of the hybridization. The hybridization portion of the hybridizing nucleic acids is at least 15 nucleotides in length and at least 80% identical to the sequence if SEQ ID No:2.

In one embodiment for preliminary screening for homologous nucleic acids, low stringency hybridization conditions, corresponding to a Tm of 55° C., can be used, (e.g., 5 times SSC, 0.1% SDS, 0.25% milk, and no formamide; or 30% formamide, 5 times SSC, 0.5% SDS). Moderate stringency hybridization conditions correspond to a higher Tm, e.g., 40% formamide, with 5 times or 6 times SSC. High stringency hybridization conditions correspond to the highest Tm e.g., 50% formamide, 5 times or 6 times SSC.

Hybridization requires that the two oligonucleic acids contain complementary sequences, although depending on the stringency of the hybridization, mismatches between bases are possible. The appropriate stringency for hybridizing oligonucleic acids depends on the length of the oligonucleic acids and the degree of complementation, variables well known in the art. For hybridization with shorter oligonucleic acids, i.e., oligonucleotides, the position of mismatches becomes more important, and the length of the oligonucleotide determines its specificity (see Sambrook et al., 11.7-11.8). In one embodiment the length for a hybridizable oligonucleic is at least about 10 nucleotides.

In a specific embodiment, the hybridization conditions are as described in the methods section: step 1—94° C.—4 minutes, step 26—40 cycles of 94° C. for 30 seconds, 42° C. for 60 seconds, 72° C. for 20 seconds and step 3—72° C. for 5 minutes.

The polymerization is catalyzed by a DNA-Taq-Polymerase in the presence of four deoxynucleotide triphosphates, one of which is radioactive, or nucleotide analogs to produce double-stranded DNA molecules. The double strands are then separated by any denaturing method including physical, chemical or enzymatic.

Commonly, the method of physical denaturation is used involving heating the oligonucleic, typically to temperatures from about 80° C. to 105° C. for times ranging from less than 1 to 10 minutes. The process is repeated for the desired number of cycles.

The resulting amplified product is subjected to gel electrophoresis or other size separation techniques and may be detected by ethidium bromide staining (Sambrook, et al., 1989).

Detection of the resulting bands is usually accomplished by exposure of the gel to X-ray film (autoradiography). The amplified products that are obtained from the sample is compared to amplified products from healthy samples and from patient with hematological malignancy, so as to detect the presence or the absence of hematological malignancy in the subject.

EXAMPLES

Experimental Procedures
Immunohistochemistry:

Immunohistochemistry was done using Histostain plus-Kit (Zymed) according to manufacturers instructions, with anti-ARTS specific primary antibodies.
Bone Marrow Sampling:

Bone marrow samples were taken from leukemic patients or people at diagnosis of other pathological states as a part of their medical assessment. Small portion of those samples were used for ARTS staining.
RNA DNA Isolation:

RNA was isolated using Tri-Reagent (MRC), DNA from blood samples was isolated using DNA isolation kit (Boehringer-Mannheinl).
Apoptosis Assays:

Detection of apoptotic cells was done using several methods: Separation of apoptotic cells using MACS-magnetic beads system (Mitenyi-Biotec). Annexin-V conjugated to magnetic beads were incubated with cells transfected either with empty vector or with ARTS expression construct, −/+ treatment with ara-C. The apoptotic cells which were bound to the annex in-V conjugated magnetic beads were eluted from the beads according to manufacturer's instructions, and counted. Efficiency of transfection was evaluated in each experiment by counting the number of cells transfected with vector-GFP construct which were visualized using a fluorescence microscope provis AX70 (Olympus).

Caspase 3 activity assay (Boehringer-Mannheim) were used with lysates of transfected cells, according to the manufacturers' protocols. Results were read using FL-600 microplate fluorescence reader (Bio-Tek). Quantitation of apoptotic cells and immunolocalization of ARTS was performed using immunofluorescence detection; cells were blocked with 5% BSA in PBS for 30 minutes, then incubated with the indicated antibodies, followed by secondary antibodies conjugated with either fluorescein or rhodamine. After washes, a drop of DAPI containing mounting solution (Vector) was added to each slide.
Transfection Methods:

Transient transfections—Transfections of leukemic cell lines were done by electroporation—using Gene-Pulser (Bio-Rad).

Example 1

Detection of the presence of ARTS protein in bone marrow derived from acute leukemic patients and healthy controls was performed. An immunohistochemistry method was used to determine the presence of ARTS protein in bone marrow of normal controls versus bone marrow from patients with leukemia by using specific antibody to ARTS.

Samples from 12 patients with acute leukemia and 10 healthy controls were assessed for the presence of ARTS protein. The results clearly show the presence of ARTS protein in the cytoplasm of cells from the myeloid lineage in bone marrow samples derived from the healthy control. Cells of the erythroid lineage were not stained. In contrast, ARTS protein was not detected in 9 out of 12 the samples derived from the patients with acute leukemia.

Example 2

Detection of the presence of ARTS protein in bone marrow derived from acute lymphoblastic leukemic patients (ALL) and healthy control was performed.

Bone marrow samples from 11 acute lymphoblastic leukemia (ALL) diagnosed patients, and a sample from one patient with acute promyelocytic leukemia (APL) were assessed for the presence of ARTS protein. In the lymphoblasts of 9 out of the 11 ALL samples, ARTS protein was not detected. The remaining two samples showed weak presence of ARTS in their nuclei. In the APL sample, ARTS was found in the cytoplasm of the myeloblast. In contrast, in lymphocytes from peripheral blood of 10 healthy controls, ARTS protein was detected in the cytoplasm of ~50% of the lymphocytes (FIG. 1A) in all assessed samples.

In addition, in a purification of enriched CD34 stem cells of hematopoetic system, high expression of ARTS protein was detected (FIG. 1D); suggesting that the absence of ARTS in the leukemic cells is not related to their differentiation stage, but rather to their malignant state.

Example 3

ARTS RNA levels in patients with leukemia were assessed. The percentage of leukemic patients which are not expressing ARTS RNA was assessed. Samples (blood or bone marrow) diagnosed with ALL were tested for the presence or absence of ARTS RNA, using specific primers for the ORF (open reading frame) of ARTS. So far, tested 16 samples of ALL patients, out of 7 (43.7%) did not express the ARTS RNA at all, 4 (25%) showed significantly reduced amount of ARTS RNA (estimated as at least 10 fold lower amount), as compared to 7 samples from healthy or non leukemic control subjects out of which 6 (85.7%) that showed high ARTS RNA expression and one -negative. Moreover, when leukemic samples were tested for the presence of exon 6, the unique sequence which codes for the specific C' terminus of ARTS, it was found that four samples (19%) out of 21 sample derived from ALL patients did not contain this exon. Other genetic aberrations were found in the leukemic patients, like for example, one patient with intact exon 6 that had no expression of ARTS RNA transcript, or another patient which was lacking both exon 5 and 6. These exciting results strongly suggest that loss of ARTS expression, for example through mutational inactivation, provides a selective advantage to transformed leukemic cells by making them less susceptible to apoptosis. These results also strongly attest to ARTS being a novel tumor suppressive gene in leukemia.

Example 4

Experiments in cell lines have shown that introduction of ARTS into leukemic cell lines causes pronounced apoptosis.

To investigate the implications of the absence of ARTS protein in the leukemic patients, leukemic cells were transfected in vitro.

The experiment was performed in four different leukemic cell lines, AT1 and K562 which contain ARTS protein and ALL 1 and HL-60 wherein the ARTS protein is absent. After transfecting the cells with ARTS expression vector, the ability of ARTS to promote apoptosis and to affect the responses of leukemic cells to pro-apoptotic stimuli was tested.

Figure 2:
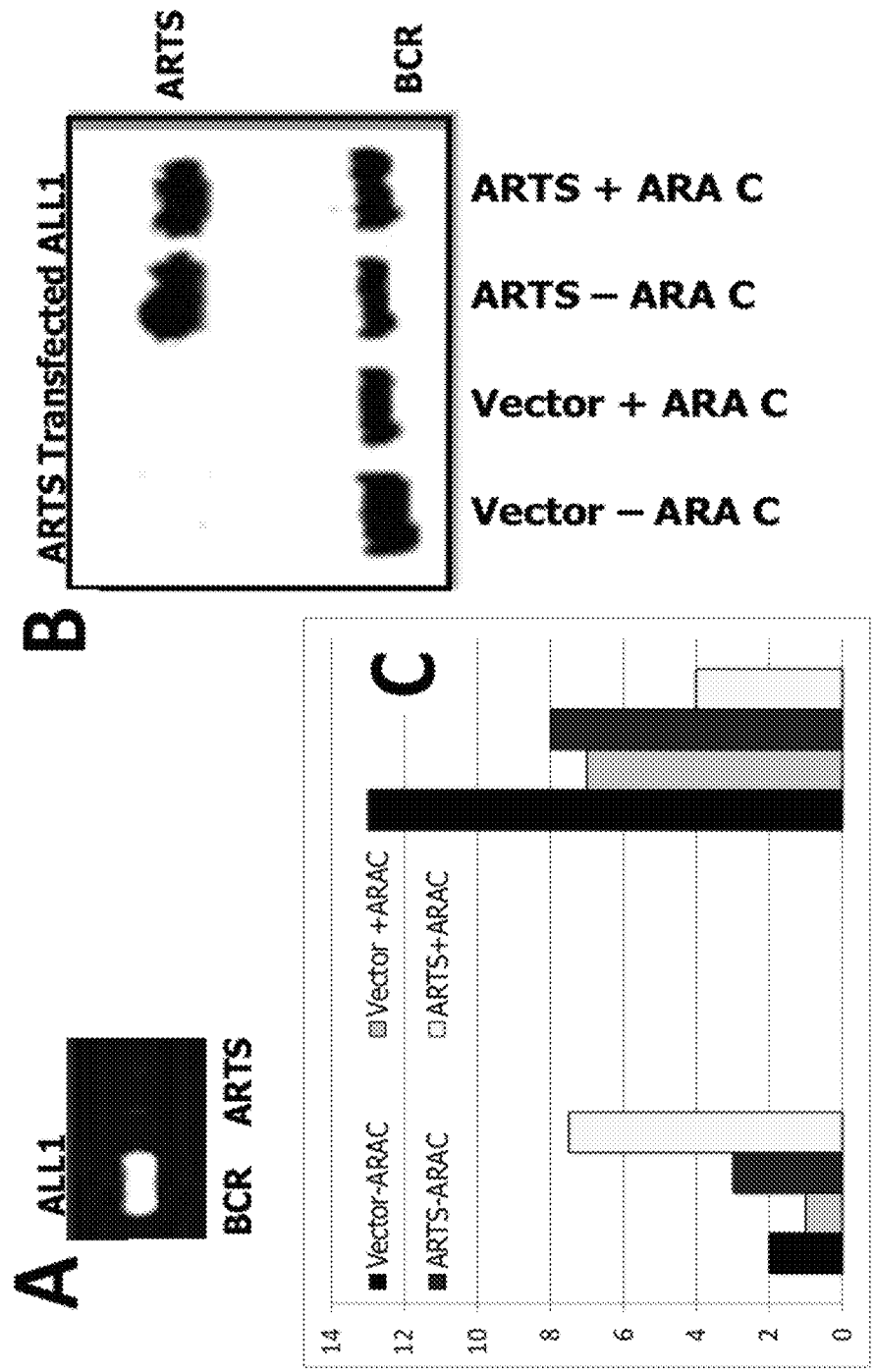
FIG. 2 shows that ALL 1 cells do not express ARTS. Reintroduction of ARTS into this cells restores apoptosis. RT-PCR results of RNA from ALL 1 cells show that although they express the control RNA BCR, they lack expression of ARTS (2A). Western blot analysis of protein lysate from ALL 1 cells showed no expression of ARTS protein in these cells (2B, two left lanes), and the appearance of ARTS protein in cells transfected with ARTS expression vector (2B, two right lanes). BCR protein showing in all lanes serves as positive and loading control.

ALL1 cells which contains the Ph+ chromosome, ATI containing the t(12:21) translocation, K562 containing the t(9:22) translocation and HI-60, containing no known genetic aberration were studies. It was found that ARTS is not expressed in ALL1 cells, both on RNA and protein level (FIG. 2A,B). Moreover, transfection of ARTS into these cells caused a dramatic induction of apoptosis, which was even increased when the ARTS transfected cells were treated with ara-C, restoring apoptotic response to these transformed cells (FIG. 2B,C).

In all experiments cells were transfected with either empty vector or ARTS containing expression vector, and tested for apoptosis following treatment with ara-C. Apoptosis was measured by counting the apoptotic fraction of cells binding to annexin-V antibody-coated beads, separated by magnetic sorter (MACS), and by testing caspase 3 activity of the transfected cells (Roche).

In all tested leukemic cell lines, there was an induction of apoptosis following ARTS overexpression.

Moreover, in both HI-60 and K562 cells, the apoptotic effect of ARTS was as high as the ara-C effect on these cells (a 2.5 to 5 fold increase in apoptosis in HL-60 and K562 cells, respectively) (FIG. 3 A,B). In all tested cells the effect of ARTS alone was at least as potent in inducing apoptosis as ara-c (FIG. 2C, FIG. 3A-C). In ALL 1 and ATI cells the effect of ARTS was even stronger than the effect of ara-C alone (FIG. 3A, FIG. 2C. In all these cells ARTS was found to induce caspase 3 activity (results shown for HL-60 cells in FIG. 3B, similar results found with other cell lines, are not presented). These results are summarized in FIG. 3. Each graph represents the average results of 3 experiments done in duplicates. In all cell lines, apoptosis was much more pronounced when the cells were both transfected with ARTS and treated with ara-C (see FIGS. 3 A,B).

To optimize the apoptotic effect of ARTS on the leulcemic cells, kinetics of apoptosis was measured 24, 36 and 48 hours after transfection, and ara-C was added for two and four hours in each time point. In k562 cells, the maximum effect of ARTS with ara-C was seen after two hours of treatment, and after four hours there was a decrease in apoptosis.

Immunohistochemistry stains with anti-ARTS specific antibody in ATI and K562 cells showed the presence of ARTS protein in both these cell lines. In addition, western blot analysis of extracts from these two cell lines confirmed the immunohistochemistry results (data not shown). Surprisingly, the HL-60 extract did not contain the ARTS protein. Further examination of HL-60 cells using RT-PCR, revealed that ARTS is also absent at the RNA level in these cells (FIG. 3D (bcr, genomic DNA and RNA were shown to be present in HL-60 cells, as positive control for the experiment). K562 and ATI, showed normal levels of ARTS RNA using RT-PCR.

It will be appreciated by persons skilled in the art that the present invention is not limited by what has been particularly shown and described herein above. Rather the scope of the invention is defined by the claims which follow:

The invention claimed is:

1. A method of predicting hematological malignancy in a subject comprising the steps of:
 [a] obtaining a sample from the subject;
 [b] obtaining cDNA from said sample;
 [c] contacting said cDNA with a specific primer for an open reading frame of nucleic acid sequence SEQ ID NO 2, so as to form a complex;
 [d] amplifying said complex so as to obtain an amplified product;
 [e] detecting said amplified product; and
 [f] comparing said amplified product level to predetermined amplified product level derived from samples from healthy subjects, thereby diagnosing the presence of hematological malignancy in said subject.

2. The method of claim 1, wherein said sample comprises a cell selected from the group consisting of: a lymphocyte cell, a bone marrow cell or a stem cell.

3. The method of claim 1, wherein the hematological malignancy is an acute leukemia, a myeloid lineage, or an acute lymphoblastic leukemia.

4. The method of claim 1, wherein step (e) further comprises the step of separating said amplified product.

5. The method of claim 1, wherein said step of separating further comprising the step of visualizing said amplified product.

6. A method of predicting hematological malignancy in a subject comprising the steps of:
 [a] obtaining a sample from the subject;
 [b] contacting said sample with an antibody directed to an epitope specific to at least a peptide of amino acid sequence SEQ ID NO 1, thereby to form an antigen-antibody complex;

[c] detecting the an antigen-antibody complex level, thereby determining the level of said amino acid sequence SEQ ID NO 1 in said sample;

[d] comparing said level of said amino acid sequence SEQ ID NO 1 to predetermined level of said amino acid sequence SEQ ID NO 1, in samples derived from healthy subjects, thereby diagnosing the presence of hematological malignancy in the subject.

7. The method of claim 6, wherein said sample comprises a cell selected from the group consisting of: a lymphocyte cell, a bone marrow cell or a stem cell.

8. The method of claim 6, wherein the hematological malignancy is acute leukemia, myeloid lineage, or acute lymphoblastic leukemia or any other subtype of leukemia.

* * * * *

SEQUENCE LISTING

```
<160> NUMBER OF SEQ ID NOS: 9

<210> SEQ ID NO 1
<211> LENGTH: 274
<212> TYPE: PRT
<213> ORGANISM: Human

<400> SEQUENCE: 1

Met Ile Lys Arg Phe Leu Glu Asp Thr Thr Asp Asp Gly Glu Leu Ser
1               5                   10                  15

Lys Phe Val Lys Asp Phe Ser Gly Asn Ala Ser Cys His Pro Pro Glu
            20                  25                  30

Ala Lys Thr Trp Ala Ser Arg Pro Gln Val Pro Glu Pro Arg Pro Gln
        35                  40                  45

Ala Pro Asp Leu Tyr Asp Asp Asp Leu Glu Phe Arg Pro Pro Ser Arg
    50                  55                  60

Pro Gln Ser Ser Asp Asn Gln Gln Tyr Phe Cys Ala Pro Ala Pro Leu
65                  70                  75                  80

Ser Pro Ser Ala Arg Pro Arg Ser Pro Trp Gly Lys Leu Asp Pro Tyr
                85                  90                  95

Asp Ser Ser Glu Asp Asp Lys Glu Tyr Val Gly Phe Ala Thr Leu Pro
            100                 105                 110

Asn Gln Val His Arg Lys Ser Val Lys Lys Gly Phe Asp Phe Thr Leu
        115                 120                 125

Met Val Ala Gly Glu Ser Gly Leu Gly Lys Ser Thr Leu Val Asn Ser
    130                 135                 140
```

```
Leu Phe Leu Thr Asp Leu Tyr Arg Asp Arg Lys Leu Leu Gly Ala Glu
145                 150                 155                 160

Glu Arg Ile Met Gln Thr Val Glu Ile Thr Lys His Ala Val Asp Glu
            165                 170                 175

Glu Lys Gly Val Arg Leu Arg Leu Thr Ile Val Asp Thr Pro Gly Phe
            180                 185                 190

Gly Asp Ala Val Asn Asn Thr Glu Cys Trp Lys Pro Val Ala Glu Tyr
            195                 200                 205

Ile Asp Gln Gln Phe Glu Gln Tyr Phe Arg Asp Glu Ser Gly Leu Asn
        210                 215                 220

Arg Lys Asn Ile Gln Asp Asn Arg Val His Cys Cys Leu Tyr Phe Ile
225                 230                 235                 240

Ser Pro Phe Gly His Gly Tyr Gly Pro Ser Leu Arg Leu Leu Arg Pro
            245                 250                 255

Pro Gly Ala Val Lys Gly Thr Gly Gln Glu Leu Ile Gln Gly Gln Gly
            260                 265                 270

Cys His

<210> SEQ ID NO 2
<211> LENGTH: 825
<212> TYPE: DNA
<213> ORGANISM: Human

<400> SEQUENCE: 2
atgatcaagc gtttcctgga ggacaccacg gatgatggag aactgagcaa gttcgtgaag      60
gatttctcag gaaatgcgag ctgccaccca ccagaggcta agacctgggc atccaggccc     120
caagtcccgg agccaaggcc ccaggccccg gacctctatg atgatgacct ggagttcaga     180
cccccctcgc ggccccagtc ctctgacaac cagcagtact tctgtgcccc agcccctctc     240
agcccatctg ccaggcccCg cagcccatgg ggcaagcttg atccctatga ttcctctgag     300
gatgacaagg agtatgtggg ctttgcaacc ctccccaacc aagtccaccg aaagtccgtg     360
aagaaaggct tgactttac cctcatggtg gcaggagagt ctggcctggg caaatccaca     420
cttgtcaata gcctcttcct cactgatctg taccgggacc ggaaacttct tggtgctgaa     480
gagaggatca tgcaaactgt ggagatcact aagcatgcag tggacataga agagaagggt     540
gtgaggctgc ggctcaccat tgtggacaca ccaggttttg gggatgcagt caacaacaca     600
gagtgctgga gcctgtggc agaatacatt gatcagcagt ttgagcagta tttccgagac     660
gagagtggcc tgaaccgaaa gaacatccaa gacaacaggg tgcactgctg cctgtacttc     720
atctcacccc tcggccatgg gtatggtcca agcctgaggc tcctggcacc accgggtgct     780
gtcaagggaa caggccaaga gcaccagggg cagggctgcc actag                      825

<210> SEQ ID NO 3
<211> LENGTH: 10
<212> TYPE: PRT
<213> ORGANISM: Human

<400> SEQUENCE: 3

Leu Pro Asn Gln Val His Arg Lys Ser Val
1               5                   10

<210> SEQ ID NO 4
<211> LENGTH: 10
<212> TYPE: PRT
<213> ORGANISM: Human

<400> SEQUENCE: 4
```

```
Lys Lys Gly Phe Asp Phe Thr Leu Met Val
1               5                   10

<210> SEQ ID NO 5
<211> LENGTH: 10
<212> TYPE: PRT
<213> ORGANISM: Human

<400> SEQUENCE: 5

Leu Val Asn Ser Leu Phe Leu Thr Asp Leu
1               5                   10

<210> SEQ ID NO 6
<211> LENGTH: 9
<212> TYPE: PRT
<213> ORGANISM: Human

<400> SEQUENCE: 6

Met Ile Lys Arg Phe Leu Glu Asp Thr
1               5

<210> SEQ ID NO 7
<211> LENGTH: 10
<212> TYPE: PRT
<213> ORGANISM: Human

<400> SEQUENCE: 7

Asp Phe Ser Gly Asn Ala Ser Cys His Pro
1               5                   10

<210> SEQ ID NO 8
<211> LENGTH: 8
<212> TYPE: PRT
<213> ORGANISM: Human

<400> SEQUENCE: 8

Pro Glu Ala Lys Thr Trp Ala Ser
1               5

<210> SEQ ID NO 9
<211> LENGTH: 6
<212> TYPE: PRT
<213> ORGANISM: Human

<400> SEQUENCE: 9

Lys His Ala Val Asp Ile
1               5
```